United States Patent [19]

Hope

[11] Plant 4,307

[45] Sep. 26, 1978

[54] KALANCHOE PLANT

[75] Inventor: Claude Hope, Cartago, Costa Rica

[73] Assignee: Mikkelsens, Inc., Ashtabula, Ohio

[21] Appl. No.: 823,852

[22] Filed: Aug. 11, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Beall & Jeffery

[57] ABSTRACT

A new asexually reproduced kalanchoe characterized by its double crenate green oblong to elliptical foliage, branching at many of the leaf axils, peduncles of the inflorescence and individual flower pedicels being small in diameter but distinctly wiry and stiff, uniform flowering and very floriferous with orange red flowers, with both the foliage and flowers possessing outstanding keeping qualities.

1 Drawing Figure

The present invention relates to a new and distinctive variety of kalanchoe plant, botanically known as Kalanchoe, and known by the cultivar name Rhumba. The new cultivar was developed by me through controlled breeding by crossing a fourth generation seedling selection of Red Empress (unpatented) as the seed parent with a second generation seedling (unpatented) originating from a cross of Brilliant Star with Swiss Rose as the pollen parent. Asexual reproduction of stem cuttings has shown that the unique features of this new kalanchoe are stabilized and are reproduced true to type in successive propagations.

The following characteristics distinguish the new kalanchoe from both its parent varieties and other cultivated kalanchoes of this type known and used in the floriculture industry:

1. In comparison to the varieties used for parentage purposes, my new cultivar has foliage that resembles Brilliant Star, the self branching typical of Swiss Rose and flower color and size similar to Red Empress, with earliness of flowering related to all three genotypes.

2. Flower color is a clear orange red with the throat being a light orange; very little fading occurs so that the color of the inflorescence remains uniform, colorful, and attractive; the flower color is more intense than the variety Brilliant Star (from seed) or the cultivar Morning Star (not patented). Flower size of my new cultivar is smaller than those of Rotkappchen, U.S. Plant Pat. No. 3,851, of Sirius, disclosed in pending U.S. application Ser. No. 709,282 of Adolf Grob. Flower response size, and quantity, are very comparable to the cultivar Pixie, disclosed in pending U.S. application Ser. No. 766,737, now U.S. Plant Pat. No. 4,209 of James C. Mikkelsen, but the flower color of Pixie is deep orange-red. Both my new cultivar and Pixie have Red Empress as a common parent, but other than the flower comparison, there are no other significant similarities between Rhumba and Pixie.

3. The inflorescence of my new cultivar is massive, and made up of an abundance of individual flowers 15 mm. in diameter, a particularly unique quality being the depth of the inflorescence, nearly two-thirds of the diameter. The total flower placement of my new cultivar has greater eye appeal than that of Morning Star.

4. My new cultivar has extremely good shelf life, a feature important for distribution and the ultimate consumer. The keeping qualities are far superior to the seed variety Red Empress, especially as to foliage.

5. Several years of testing have demonstrated that my new cultivar can be readily produced in 9 cm. or 12 cm. or 15 cm. pots with remarkably uniform and dependable quality.

6. The testing and development program has also shown that Rhumba can be produced equally well as a pinched plant or a non-pinched plant, thereby allowing the grower a wider range of plant forms.

7. A very distinguishing characteristic of my new cultivar is the relatively thin but stiff, wiry flower stems and individual flower pedicels, an excellent quality for shipping.

8. Unlike most kalanchoe cultivars, the inflorescence of my new cultivar has a placement very noticeably above the foliage, which tends to remain basal.

9. The foliage is attractive, long, elliptical, double crenate with deep indentations toward a tendency to be lobed; basal and cascading; has better keeping qualities than Rotkappchen or Siruis, but similar to the cultivar Morning Star.

10. Early uniform flowering occurs in as little as 60 days in late spring, summer, and early fall and up to 77 days during the reduced light period of winter.

The accompanying colored photograph illustrates the overall appearance of my new cultivar, and shows the colors as true as it is reasonably possible to obtain in a colored reproduction of this type. The plant illustrated in the colored photograph was propagated in a 5 cm. plastic pot; repotted into a 12 cm. clay pot Apr. 4, 1977. After removing the apical tip on Apr. 19, 1977, the plant was placed into short day treatment the same day and the first open flowers were recorded on June 12, 1977. The photograph was taken June 28, 1977, the plant at that time having an inflorescence 26 cm. to 28 cm. in diameter, vertical flowering being approximately 15 cm. high. The total plant height was 32 cm. above the pot. The detailed descriptions which follow are based on this illustrated plant.

The following is a detailed description of my new kalanchoe variety based on plants produced under commercial practices in Costa Rica and Ashtabula, Ohio. Color references are made to the Royal Horticultural Society Colour Chart except where general terms of ordinary dictionary significance are used.

Parentage: The seed parent was a selected fourth generation seedling out of my controlled inbreeding of Red Empress which was crossed with a second generation seedling that originated from a controlled cross of Brilliant Star with Swiss Rose as the pollen parent.

Propagation:

(A) *Type cutting.*—Terminal stems rooted in 5 cm. plastic pots.

(B) *Time to root.*—15–18 days at 22° C. summer; 18–22 days at 21° C. winter.

(C) *Rooting habit.*—Profuse, dendritic, fibrous.

Plant description:

(A) *Form.*—Stiff, upright, compact basal foliage, close internodes; a definite gap appears between top of the foliage and the beginning of flowering.

(B) *Habit of growth.*—Vigorous rate of growth, being more rapid than the Bull or Wyss cultivars to date.

(C) *Foliage.*—Generally, green, convex, cascading, close internode, large foliage. (1) Size: Up to 6–8 cm. wide by 12–15 cm. long, petiole 2 cm., base obtuse, apices normally acute with some tendency to obtuse. (2) Shape: Oblong to elliptical. (3) Texture: Glabrous, coriacious, thick, rigid. (4) Margin: Strongly double crenate to lobed. (5) Color: Mature foliage top side, green 137A; underside yellow green 148-B.

Flowering description:

(A) *Flowering habits.*—Flowers open uniformly in 10–15 days, inflorescence being in the form of paniculate cymes up to 26 cm. to 28 cm. in diameter and up to 15 cm. in vertical height, flowering continuously for 12–15 weeks.

(B) *Natural flowering season.*—Under good light conditions at 19°–20° C. flowering occurs in late December; under poor light at 20° C. early to mid-January. Flowering time under controlled day length at 22° C in summer is 60 days; in winter is 77 days. Flowering varies considerably depending mostly on daylight intensity and duration relative to temperatures.

(C) *Flower buds.*—Typical kalanchoe flower buds with petals swirled before opening, pointed, 12 mm. long, 2 mm. in diameter, pedicel 2 mm., length of bud up to 15 mm. when open.

(D) *Flowers borne.*—Individual flowers are on a short, stiff pedicel branching from secondary thin stiff peduncles which in turn are carried on primary peduncles originating from the leaf axils; total inflorescence paniculate cyme.

(E) *Quantity of flowers.*—Terminal cymes up to 150 flowers, secondary laterals 75–100 flowers. The illustration has an estimated 600 flowers; considered highly floriforous.

(F) *Petals.*—(1) Shape: Broad elliptical to oval, usually pointed. (2) Color top side when opening, orange red 30C, fading slightly to 30D; under side 28-C, (3) Number of petals: 4, nearly separated, 5 mm. wide by 7–8 mm. long, flower diameter 15 mm.

(G) *Reproductive organs.*—(1) Stamens: Eight in number. (a) Anther shape: Flat anvil, color dark brown. (b) Filament color: Light translucent yellow. (c) Pollen color: Dark yellow/tan. (2) Pistels: (a) Stigma shape: 4 stigmas, coalesced to irregular crystalline, color translucent green. (b) Style color: Translucent light yellow. (c) Ovaries: Four in number, 6 mm. before pollinated, color green.

Disease Resistance: No diseases of commercial concern have been noted to date.

I claim

1. A new and distinct cultivar of kalanchoe plant known by the cultivar name of Rhumba and particularly characterized as to uniqueness by the combined characteristics of clear orange red flower color, with the throat being light orange; massive inflorescence, having substantial depth of flowering; excellent keeping qualities for both flowers and foliage; relatively thin but stiff, wiry flower stems; long, elliptical, double crenate foliage, excellent branching habit, and by its early, uniform flowering.

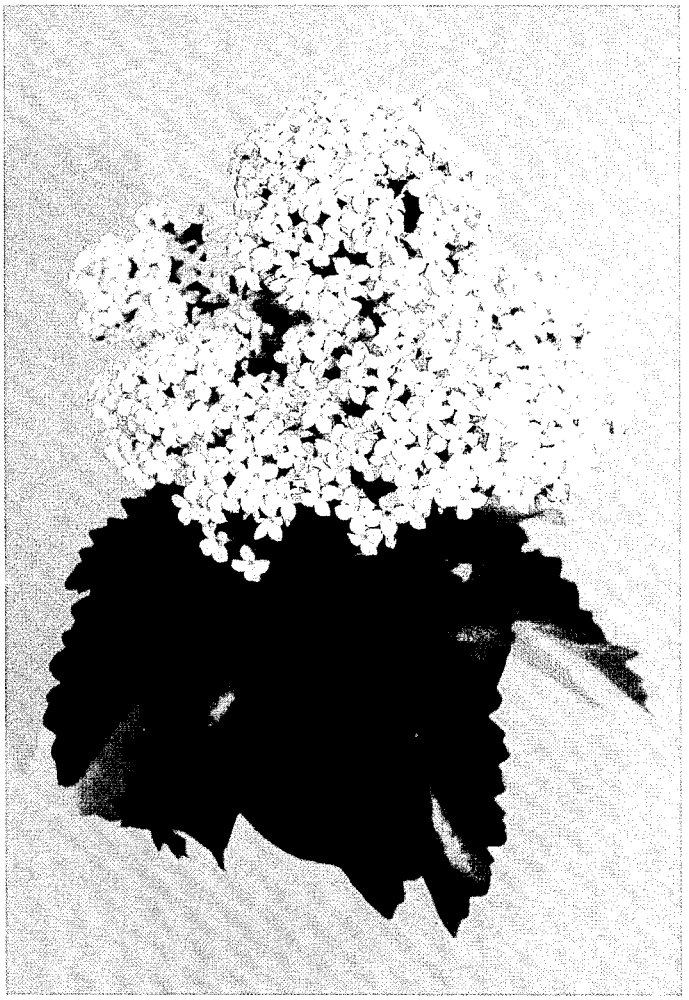

* * * * *